(12) United States Patent
Faizan et al.

(10) Patent No.: US 11,857,687 B2
(45) Date of Patent: Jan. 2, 2024

(54) APPARATUS FOR SANITISING PRODUCTS

(71) Applicant: Mirza Faizan, Irving, TX (US)

(72) Inventors: Mirza Faizan, Irving, TX (US); Mirza Rizwan, Patna (IN); Kayla Goodrich, Farmers Branch, TX (US); Manish Rangan, Frisco, TX (US); Muhammad Sayed, Irving, TX (US); Benjamin Stafford, Dallas, TX (US); Zaina Iqbal, Murphy, TX (US); Shayan Iqbal, Murphy, TX (US); Kenny Joel DeCay, Jr., Arlington, TX (US); Omar Eido, Rowlett, TX (US); Saadia Asaf, Aligarh (IN); Mansoor Hasan Khan, Aligarh (IN)

( * ) Notice: Subject to any disclaimer, the term of this patent is extended or adjusted under 35 U.S.C. 154(b) by 361 days.

(21) Appl. No.: 17/460,187

(22) Filed: Aug. 28, 2021

(65) Prior Publication Data
US 2023/0066405 A1   Mar. 2, 2023

(51) Int. Cl.
*A61L 2/10*   (2006.01)
*B65G 43/10*   (2006.01)
*B65G 45/22*   (2006.01)
*A23L 3/28*   (2006.01)
*A23L 3/00*   (2006.01)
*A61L 2/22*   (2006.01)
*A23L 3/3589*   (2006.01)

(52) U.S. Cl.
CPC .............. *A61L 2/10* (2013.01); *A23L 3/001* (2013.01); *A23L 3/003* (2013.01); *A23L 3/28* (2013.01); *A23L 3/3589* (2013.01); *A61L 2/22* (2013.01); *B65G 43/10* (2013.01); *B65G 45/22* (2013.01); *A23V 2002/00* (2013.01); *A61L 2202/11* (2013.01); *A61L 2202/121* (2013.01); *A61L 2202/122* (2013.01); *A61L 2202/14* (2013.01)

(58) Field of Classification Search
CPC .......... A61L 2/10; A61L 2/22; A61L 2202/11; A61L 2202/121; A61L 2202/122; A61L 2202/14; A23L 3/001; A23L 3/28; A23L 3/00; A23L 3/3589; B65G 43/10; B65G 45/22; A23V 2002/00
USPC ........................... 250/453.11, 454.11, 455.11
See application file for complete search history.

(56) References Cited

U.S. PATENT DOCUMENTS

2022/0007763 A1\*   1/2022   Masna ................ A61B 5/7267

FOREIGN PATENT DOCUMENTS

IN   202011027891   \*   8/2020   ............. A61L 2/10

\* cited by examiner

*Primary Examiner* — Nicole M Ippolito

(57) ABSTRACT

An apparatus for sanitising products comprising a housing comprising a bottom portion, interior walls an external portion and doors a pair of support beams, a plurality of internal conveyor belts, at least one UV-C light connected inside the housing, a first opening adapted to allow products to enter the housing for sanitisation and a second opening adapted to allow products to exit the housing after sanitisation.

10 Claims, 3 Drawing Sheets

APPARATUS FOR SANITISING PRODUCTS

FIELD OF THE INVENTION

The present invention relates to an apparatus for sanitising products.

BACKGROUND OF THE INVENTION

In the field of sterilization and disinfection of the surface of an object, conventional modes such as chemical sterilization and ultraviolet lamp sterilization are mainly adopted. The chemical sterilization and disinfection modes mainly comprise alcohol sterilization and chlorine-containing sterilization and disinfection modes, and although the alcohol sterilization and disinfection can be used for quickly sterilizing and disinfecting a large area, the alcohol sterilization and disinfection modes are volatile and have potential safety hazards in storage; the chlorine-containing disinfection mode has chemical residues, and has great influence on human health and environment.

The ultraviolet lamp has a large divergence angle, and the energy distribution of light spots is uneven, so that the local killing effect is poor, and objects carrying bacterial viruses cannot be rapidly and effectively killed.

Conventionally, conveyor systems for disinfecting products, including packaging products, containers, lids, bottles, consumer products, toys and food products, can overheat, dry, or change the properties of the products, resulting in a critical property change or increase bacteria or pathogen growth or an undesirable change in the product due to exposure to elevated temperatures as well as over exposure to technology intervention. For example, a bread product moving through a disinfecting conveyor may be heated from an ultraviolet (UV) light source, thereby creating on increasing bacteria and or changing the quality texture, dryness of the bread. In addition, bacteria may grow on components of the conveyor system, such as the conveyor belt and the bacteria may be transferred to other products as they move through the conveyor.

In the prior art, an ultraviolet laser sterilization system is disclosed, in which a scanning module comprises a plurality of reflectors for receiving the ultraviolet laser and a controller for controlling the rotation of each reflector to adjust the exit angle of the ultraviolet laser, so as to allow the ultraviolet laser to enter the controller.

A conveyor-belt checkout stand may be used to transport groceries or other items toward the cashier and away from the cashier to the bagging area. In a conveyor-belt type checkout stand, a synthetic conveyor belt, typically of rubber or plastic, is supported on each end by a roller. These rollers provide a tension between themselves to retain the conveyor belt in position. The belt is also equipped with a drive motor that advances the belt around the rollers. In use, a customer approaches a checkout stand and places his groceries or other items on the conveyor belt. Either by manual control or by an automated device, the rollers begin to rotate, thereby advancing the surface of the conveyor belt containing the groceries or other items toward the cashier. Sterilizing systems for sterilizing the conveyor belt may be provided to maintain a sanitary environment.

Furthermore, since ultraviolet radiation is harmful to the eye, the conventional apparatus described above is provided with curtains, each comprising a plurality of strips hung from the openings to the entrance and exit, through which the conveyor passes to travel through the sterilization chamber. However, when the products are conveyed in and out of the sterilization chamber, they force the aforementioned curtains aside and allow ultraviolet radiation to leak from the gaps between the curtain strips. As a result, the eyes of the operator handling the products are exposed to ultraviolet rays. Accordingly, there is need of a sterilizing apparatus capable of completely shutting out ultraviolet radiation from the outside during handling.

U.S. Pat. No. 4,877,964A discloses an ultraviolet sterilizing apparatus comprising: a sterilization chamber defining an enclosed space and having an entrance and an exit; a roller conveyor including a number of rollers arranged between the entrance and the exit for conveying products to be sterilized through the interior of said sterilization chamber along a conveyance path; a plurality of first sterilizing ultraviolet lamps arranged about the conveyance path; and a plurality of second sterilizing ultraviolet lamps situated below the conveyance path, each of said second ultraviolet lamps being interposed between mutually adjacent ones of said rollers and arranged at a level lower than that of a conveyance plane of said roller conveyor.

EP2678255A1 discloses a sterilizing system for sterilizing a continuous loop conveyor belt of a conveyor system. The conveyor system includes a drive operatively connected to the conveyor belt and operative to move the belt between upper and lower flight paths. The upper flight path includes an exposed surface for receiving items. The sterilizing system includes a housing that is configured to at least partially cover the lower flight path. An ultraviolet light source is positioned in the interior of the housing. The light source is operative to emit ultraviolet light on the belt at the lower flight path to sanitize the belt.

Yet another prior art US20200297004A1 disclose a disinfecting conveyor system, which utilizes ultraviolet light to disinfect a product as it passes through an enclosure on a conveyor. A UV light sensor provides feedback to a control system that can change the amount of UV light exposure, speed of conveyor, and disinfection reaction. A UV light sensor may be a coupled to the conveyor and the UV light intensity and time of exposure within the enclosure may be used to calculate a UV light dose. A user of the system may input a required UV light dose or the type of product to be disinfected and the control system may automatically control the speed of the conveyor and/or the UV light intensity to provide the required UV dose. The system may utilize an air filtration and/or cooling system to provide a flow of clean and cool process air to the enclosure to maintain a temperature that is below a threshold temperature.

Another prior art U.S. Ser. No. 10/933,150B1 discloses conveyor belt sanitization apparatus and method for sanitizing a conveyor belt of the species commonly found at grocery stores and supermarkets using ultraviolet (UV) light. One or more UV light bulbs in the apparatus may be positioned to effectively sanitize a conveyor belt.

However, the above-cited prior arts have drawbacks. The known devices and methods to sanitize the products and objects are inefficient. In particular, as per the study, the existing devices for sanitisation are not capable of neutralising 100 percent bacteria from the objects. Thus, once the product exits the UV sanitisation device after sanitisation, the users believe that there is no virus or bacteria existing on the products. However, there are still viruses and bacteria existing. In order to ensure effective neutralisation of the virus or bacteria from the objects, it is required to provide a device for sanitisation as per an embodiment of the present invention.

Thus, there is a need to have an apparatus for sanitising products. Accordingly, there is a need to overcome the drawbacks of these prior art. The drawbacks of prior art are overcome by the present invention, as detailed in the forthcoming sections of the present application.

OBJECTS OF THE INVENTION

The main object of the present invention is to provide an apparatus for sanitising products.

Another object of the present invention is to provide an apparatus for sanitising products that effectively neutralises the viruses or bacteria present on products.

Another object of the present invention is to provide an apparatus for sanitising products that detects the presence of infection twice, once before sanitisation and once after sanitisation.

SUMMARY OF THE INVENTION

In order to solve the drawbacks of the prior art, the present invention provides an apparatus for sanitising products. According to an embodiment of the present invention, the apparatus comprises a housing comprising a bottom portion, interior walls an external portion and doors; a pair of support beams; a plurality of internal conveyor belts; at least one UV-C light connected inside the housing; a first opening adapted to allow products to enter the housing for sanitisation; and a second opening adapted to allow products to exit the housing after sanitisation.

In some embodiments, the bottom portion is adapted to be attached to the support beams.

In some embodiments, the support beams carrying the housing are placed on an external conveyor belt.

In some embodiments, the support beams carrying the housing are placed on an external conveyor belt.

In some embodiments, the external portion comprising at least one switch for controlling light, switches for moving the internal conveyor belt and switches for opening/closing the doors.

In some embodiments, the at least one light, switches for moving the internal conveyor belt and switches for opening/closing the doors are operated via remote control.

In some embodiments, the plurality of internal belts is arranged apart each other to allow seamless transfer between the plurality of internal belts.

In some embodiments, the interior walls comprise reflective strips to ensure that UV-C light can reach all angles and cavities of products.

In some embodiments, the plurality of internal belts move at a constant speed so that the products are inside the apparatus for 16 seconds for neutralizing all pathogens.

In some embodiments, the first opening and the second opening comprise black strips adapted to block users from the UV-C lights and to prevent escape of the UC-C lights.

In some embodiments, the external portion comprises angled covers adapted to block UV-c lights that pass through the rubber strips.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

Figure 1:
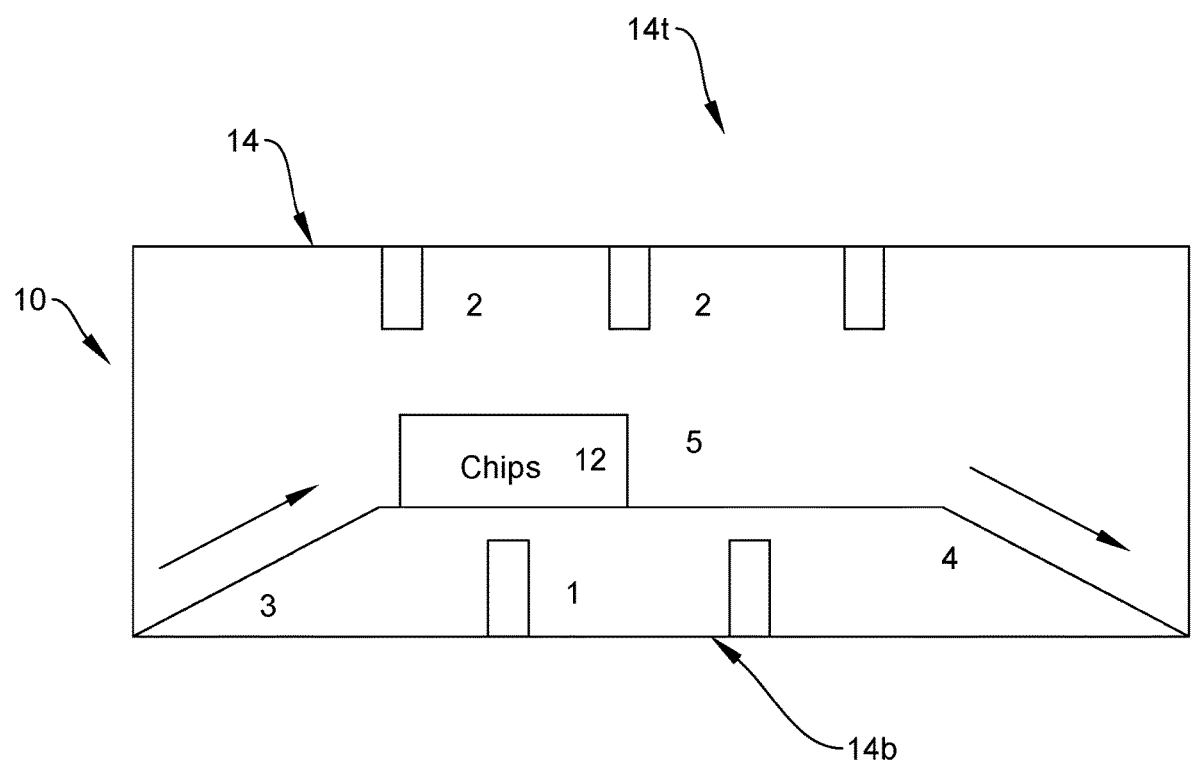
FIG. 1 is a perspective view of an apparatus for sanitising products.

Persons skilled in the art will appreciate that elements in the figures are illustrated for simplicity and clarity and may not have been drawn to scale. For example, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

DETAILED DESCRIPTION OF DRAWINGS

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which this invention belongs. The system, methods, and examples provided herein are illustrative only and not intended to be limiting.

Embodiments of the present invention will be described below in detail with reference to the accompanying drawings.

It will be understood by those skilled in the art that the foregoing general description and the following detailed description are explanatory of the invention and are not intended to be restrictive thereof.

Reference throughout this specification to "an aspect", "another aspect" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a nonexclusive inclusion, such that a process or method that comprises a list of steps does not include only those steps but may include other steps not expressly listed or inherent to such process or method. Similarly, one or more devices or subsystems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfil the requirements of uniqueness, utility and non-obviousness.

Embodiments of the present invention will be described below in detail with reference to the accompanying drawings.

FIG. 1 is a perspective view of an apparatus for sanitising products. According to an aspect of the present invention, an apparatus (10) for sanitising products (12) is disclosed. In some embodiments, the apparatus (10) comprises a housing (14) comprising a bottom portion (14b), interior walls, an external portion and doors. In some embodiments, the apparatus (10) further comprises a pair of support beams. In some embodiments, the apparatus (10) further comprises a plurality of internal conveyor belts (3, 4, 5). In some embodiments, the apparatus (10) further comprises at least one UV-C light (1, 2) connected inside the housing. In some embodiments, the apparatus (10) further comprises a first opening adapted to allow products (12) to enter the housing (14) for sanitisation. The first opening is configured with a first disinfection spray nozzle (not shown). In some embodiments, the apparatus (10) further comprises a second opening adapted to allow products to exit the housing (14) after sanitisation. The second opening is configured with a second disinfection spray nozzle (not shown).

According to an embodiment of the present invention, the housing (14) may comprise the bottom portion (14b), the top portion (14t) and side portions. The housing (14) forms a closed body with two opening on a front portion and a read portion to allow entry and exit of the products before sanitisation and after sanitisation, respectively. The housing (14) may comprise the interior walls configured with UV-C lights (1, 2) connected on the top portion and bottom portions of the interior walls. The UV-C lights (1, 2) are focused on the plurality of conveyor belts (3, 4, 5) carrying the products (12).

According to an embodiment of the present invention, the apparatus (10) further comprises the pair of support beams. When the apparatus (10) is used on a conveyor belt of a grocery store, the apparatus (10) will sit on support beams. The support beams will be placed horizontally across the existing conveyor belt of the grocery store or alike. The support beam will allow the apparatus (10) to sit above the existing conveyer belt as to not interfere with it. Thus, the apparatus (10) can be made portable such that it can be placed on any kind of conveyor belts in any market. In some embodiments, the apparatus is raised by an inch above the existing conveyor belt in order to not interfere with it. The apparatus (10) is raised by means of horizontal supports.

According to an embodiment of the present invention, the bottom portion (14b) is adapted to be attached to the support beams. The support beams carrying the housing (4) are placed on an external conveyor belt.

According to an embodiment of the present invention, the apparatus (10) further comprises a plurality of internal conveyor belts (3, 4, 5). The apparatus (10) does not require a separate conveyor belt. The apparatus (10) is provided with an internal conveyor belt system (3, 4, 5). In some embodiments, the plurality of internal belts (3, 4, 5) move at a constant speed so that the products are inside the apparatus for 16 seconds for neutralizing all pathogens. In some embodiments, the plurality of internal belts (3, 4, 5) is arranged apart each other to allow seamless transfer of products between the plurality of internal belts.

In some embodiments, the plurality of internal belts (3, 4, 5) may comprise of an entry and exit conveyor belts that run at the same speed as the middle one. In some embodiments, the apparatus (12) operates using three conveyor belts (3, 4, 5) all of which operate independently of each other. The first conveyor belt is angled and allows products (12) to be brought up to the second conveyor belt. The second conveyor belt is made from polycarbonate and is clear, this allows the conveyor belt to remain durable and allows UV-C lights (1, 2) to sanitize the bottom of products (12). The last conveyor belt is angled downward and allows groceries or products (12) to exit the apparatus (10). The conveyor belts (3, 4, 5) will be at least a centimeter apart to ensure a seamless transfer between belts (3, 4, 5).

In some embodiments, the apparatus (10) further comprises at least one UV-C light (1, 2) connected inside the housing. At least one effect can be that the apparatus (10) utilizes UV-C lights (1, 2) to eliminate pathogens, germs, and microbes on grocery items. In some embodiments, once groceries enter the apparatus (10), they will be sanitized by means of UV-C lights (1, 2) placed in the top portion (14t) and bottom portion (14b) and the products (12) will come out from the other side. This apparatus (12) is meant to sanitize the outer packaging of a product.

According to an embodiment of the present invention, the apparatus (10) utilizes UV-C lights (1, 2) to sanitize the products (12). In some embodiments, the apparatus (10) is provided with at least three UV-C light lamps installed on the ceiling (14t) of the apparatus (10), i.e., directly above the second conveyor belt. In some embodiments, the apparatus (10) is provided with at least two UV-C lights posted under the second conveyor belt. The conveyor belts (3, 4, 5) will move at a constant speed in order to ensure that the products (12) are inside the apparatus (10) for at least 16 seconds. At least one effect of this feature can be that all pathogens on the products (1) are neutralized.

According to an embodiment of the present invention, the apparatus (10) further comprises a first opening adapted to allow products (12) to enter the housing (14) for sanitisation. The first opening is configured with a first disinfection spray nozzle (not shown). The effect of the spray nozzle is that the products (12), before entering the apparatus (10), are first sanitized with a disinfection liquid so that the neutralisation of the germs is made for effective.

According to an embodiment of the present invention, the apparatus (10) further comprises a second opening adapted to allow products to exit the housing (14) after sanitisation. The second opening is configured with a second disinfection spray nozzle (not shown). The effect of the spray nozzle is that the products (12), exiting the apparatus (10) after UV-C sanitisation, are again sanitized with disinfection so that the neutralisation of the germs is optimised.

Figure 2:
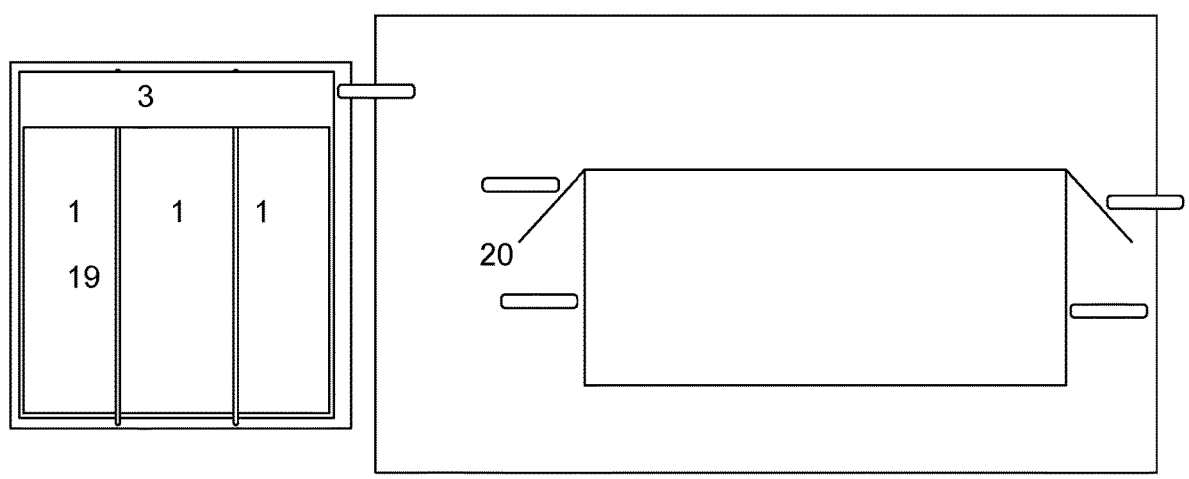
FIG. 2 is a perspective view of exit and entry portions of an apparatus for sanitising products.

FIG. 2 is a perspective view of exit and entry portions of an apparatus for sanitising products. In some embodiments, the interior walls comprise reflective strips to ensure that UV-C light can reach all angles and cavities of products. Thus, at least one effect of the reflective strips posted on the interior walls of the apparatus can be that UV-C light can reach all angles and cavities of any product that enters the apparatus.

According to an embodiment of the present invention, the first opening and the second opening comprise black strips (19) adapted to block users from the vicinity of the UV-C lights and to prevent escape of the UV-C lights. In some embodiments, the external portion comprises angled covers (20) adapted to block UV-C lights that pass through the rubber strips (19). Thus, at least one effect of this feature can be that the safety of everyone around the apparatus is ensured. In particular, at the entrance and exit of the apparatus there are black rubber strips that block and UV-C light from escaping. Further, the usage of angled covers ensures the blockage of any light that makes it past the rubber strips.

Figure 3:
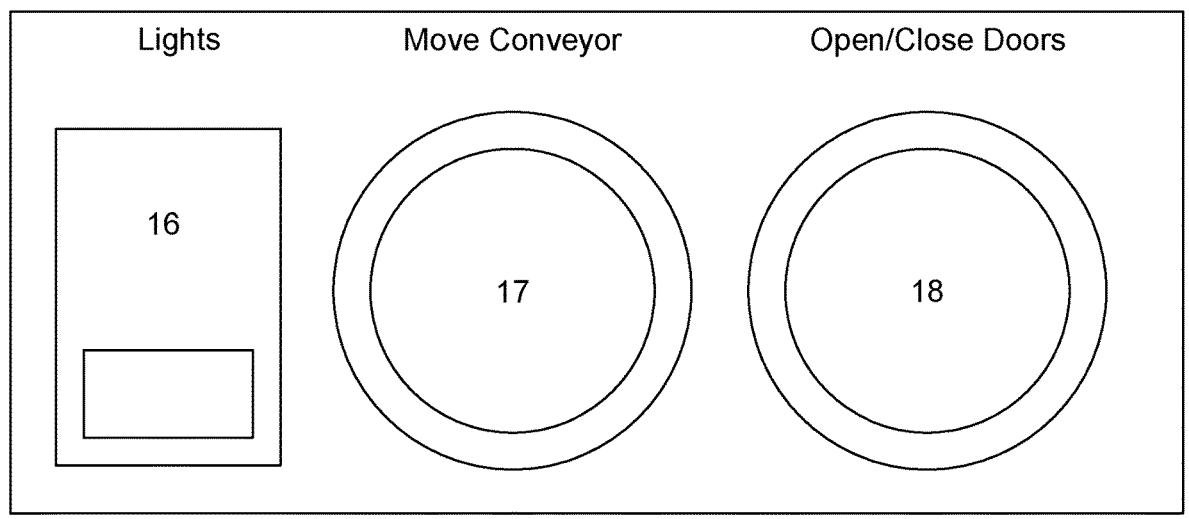
FIG. 3 is a perspective view of a remote-control operation for an apparatus for sanitising products.

FIG. 3 is a perspective view of a remote-control operation for an apparatus for sanitising products. According to an embodiment of the present invention, the external portion comprising at least one switch (16) for controlling lights. In some embodiments, the external portion further comprises switches (17) for moving the internal conveyor belts. In some embodiments, the external portion further comprises switches (18) for opening/closing the doors. According to an embodiment of the present invention, the at least one light (16), switches (17) for moving the internal conveyor belts and switches (18) for opening/closing the doors are operated via network. In some embodiments, the network may be formed to provide an effect of remote control. In some embodiments, the network may be formed to provide an effect of automatic control.

Moreover, the actions of any components in the block diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

While specific language has been used to describe the present subject matter, any limitations arising on account thereto, are not intended. As would be apparent to a person in the art, various working modifications may be made to the method in order to implement the inventive concept as taught herein. The drawings and the foregoing description give examples of embodiments.

What is claimed is:

1. An apparatus (10) for sanitising products (12) comprising:
   a. a housing (14) comprising a bottom portion (14b), interior walls, an external portion and doors;
   b. a pair of support beams;
   c. a plurality of internal conveyor belts (3, 4, 5);
   d. at least one UV-C light (1, 2) connected inside the housing;
   e. a first opening, configured with a first disinfection spray nozzle, adapted to allow products (12) to enter the housing (14) for sanitisation; and
   f. a second opening, configured with a second disinfection spray nozzle, adapted to allow products to exit the housing (14) after sanitisation.

2. The apparatus (10) for sanitising products (12) as claimed in claim 1, wherein the bottom portion (14b) is adapted to be attached to the support beams.

3. The apparatus (10) for sanitising products (12) as claimed in claim 1, wherein the support beams carrying the housing (4) are placed on an external conveyor belt.

4. The apparatus (10) for sanitising products (12) as claimed in claim 1, wherein the external portion comprising at least one switch (16) for controlling lights, switches (17) for moving the internal conveyor belts (3, 4, 5) and switches (18) for opening/closing the doors.

5. The apparatus (10) for sanitising products (12) as claimed in claim 4, wherein the at least one light (16), switches (17) for moving the internal conveyor belts (3, 4, 5) and switches (18) for opening/closing the doors are operated via remote control.

6. The apparatus (10) for sanitising products (12) as claimed in claim 1, wherein the plurality of internal belts (3, 4, 5) is arranged apart each other to allow seamless transfer of products between the plurality of internal belts.

7. The apparatus (10) for sanitising products (12) as claimed in claim 1, wherein the interior walls comprise reflective strips to ensure that UV-C light can reach all angles and cavities of products.

8. The apparatus (10) for sanitising products (12) as claimed in claim 1, wherein the plurality of internal belts move at a constant speed so that the products are inside the apparatus for 16 seconds for neutralizing all pathogens.

9. The apparatus (10) for sanitising products as claimed in claim 1, wherein the first opening and the second opening comprise black strips (19) adapted to block users from the vicinity of the UV-C lights (1, 2) and to prevent escape of the UV-C lights (1,2).

10. The apparatus (10) for sanitising products (12) as claimed in claim 9, wherein the external portion comprises angled covers (20) adapted to block UV-C lights that pass through the rubber strips (19).

* * * * *